United States Patent

Sicken

Patent Number: 5,728,746
Date of Patent: Mar. 17, 1998

[54] PROCESS FOR THE PREPARATION OF MIXTURES OF OLIGOMERIC PHOSPHORIC ACID ESTERS AND THEIR USE AS FLAMEPROOFING AGENTS FOR POLYURETHANE FOAMS

[75] Inventor: Martin Sicken, Cologne, Germany

[73] Assignee: Hoechst Aktiengesellschaft, Frankfurt am Main, Germany

[21] Appl. No.: 736,360

[22] Filed: Oct. 23, 1996

[30] Foreign Application Priority Data

Nov. 3, 1995 [DE] Germany .................. 195 40 861.6

[51] Int. Cl.$^6$ .................. C08G 18/04; C07F 9/02
[52] U.S. Cl. .............. 521/169; 252/182.14; 252/182.24; 252/182.3; 521/155; 521/168; 524/710; 528/72; 558/70; 558/113; 558/114
[58] Field of Search .................. 521/108, 155, 521/168, 169; 252/182.14, 182.15, 182.24, 182.28, 182.3; 558/70, 113, 114; 524/710; 528/72

[56] References Cited

U.S. PATENT DOCUMENTS 3,764,640  10/1973  Klose .................. 521/108

FOREIGN PATENT DOCUMENTS

| 2136770 | 6/1995 | Canada. |
| 251 249 | 1/1988 | European Pat. Off.. |
| 658 561 | 6/1995 | European Pat. Off.. |
| 2 036 587 | 2/1972 | Germany. |
| 2036587 | 2/1973 | Germany. |
| 4342972 | 6/1995 | Germany. |

Primary Examiner—John M. Cooney, Jr.
Attorney, Agent, or Firm—Connolly and Hutz

[57] ABSTRACT

The invention relates to a process for the preparation of mixtures of oligomeric phosphoric acid esters of the formula (I)

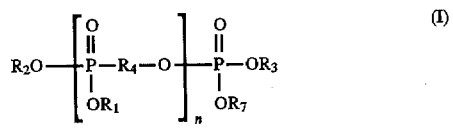

in which n is a number from 0 to 8, $R_1$, $R_2$, $R_3$ and $R_7$ are identical or different and are a halogen-free alkyl or aryl radical or a hydroxyl-containing radical of the formula II and $R_4$ is a radical of the formula III

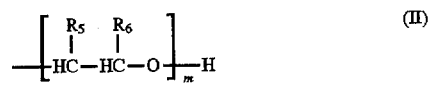

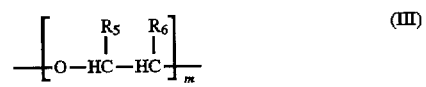

in which, in the formulae II and III, $R_5$ and $R_6$ are a hydrogen atom or an alkyl radical and m is a number from 1 to 4, which comprises reacting, in a first stage, aliphatic or araliphatic alcohols and/or phenols with phosphorus pentoxide ($P_4O_{10}$) in a molar ratio of (2.8 to 6.0):1.0 (alcohol/phenol: $P_4O_{10}$) at a temperature from 20° to 100° C. in the course of 0.5 to 72 hours, a polyphosphoric acid partial ester mixture of the formula V

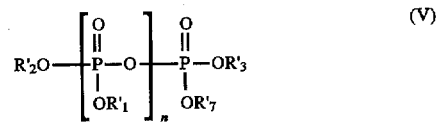

which $R_1'$, $R_2'$, $R_3'$ and $R_7'$ are an alkyl or aryl radical or H, being obtained, and, in a second stage, reacting this mixture with an epoxide of the formula (IV)

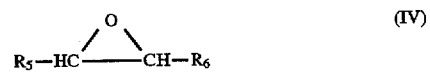

at a temperature of 20°–180° C.

The invention also relates to the use of the mixtures prepared by this process as flameproofing agents for polyurethanes.

12 Claims, No Drawings

PROCESS FOR THE PREPARATION OF MIXTURES OF OLIGOMERIC PHOSPHORIC ACID ESTERS AND THEIR USE AS FLAMEPROOFING AGENTS FOR POLYURETHANE FOAMS

The invention relates to a process for the preparation of mixtures of oligomeric phosphoric acid esters of the formula (I)

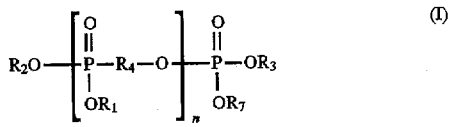

in which n is a number from 0 to 8, $R_1$, $R_2$, $R_3$ and $R_7$ are identical or different and are a halogen-free alkyl or aryl radical or a hydroxyl-containing radical of the formula (II) and $R_4$ is a radical of the formula (III)

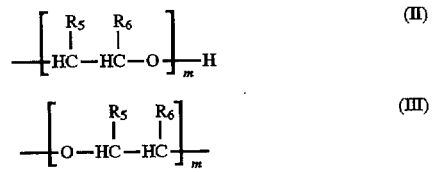

in which, in the formulae (II) and (III), $R_5$ and $R_6$ are a hydrogen atom or an alkyl radical and m is a number from 1 to 4, and to the use of the phosphoric acid esters thus prepared.

Polyurethane foams are widely employed for the most diverse uses. In fields of use which impose high requirements on the burning properties of the materials contained therein (for example interior trim in automobiles, building insulations, electrical/electronic engineering), the use of polyurethanes and polyisocyanurates is possible only with the aid of added flameproofing agents. The flameproofing agents employed are chiefly the chlorine-containing phosphoric acid esters tris(2-chloroethyl) phosphate (TCEP), tris(chloroisopropyl) phosphate (TCPP) and tris(2,3-dichloropropyl) phosphate (TDCPP), and bromine-containing products, such as dibromoneopentylglycol and brominated polyols. These products have the common feature that, in order to achieve the required flameproofing effectiveness, they comprise halogens in bonded form as an essential constituent. This is a disadvantage since, in the event of a fire, halogen-containing products evolve corrosive hydrogen halides, which are often the cause of secondary damage which can exceed the actual fire damage severalfold. Furthermore, halogenated products show severe evolution of smoke in the event of a fire.

The product group mentioned first furthermore has the disadvantage that they are incorporated merely physically as additive flameproofing agents, which means that partial emigration thereof can take place, for example, under exposure to heat. This adverse effect, which plays a considerable role in the case of open-cell foams in particular, not only causes a subsidence of the flame-proofing action with time and therefore an increase in the amount of flameproofing agent to be employed, but also leads to contamination of the environment of the products and to undesirable changes to the surface of the materials. Thus, for example, such additive additions contribute toward the so-called "fogging", the condensation of evaporated volatile constituents from the motor vehicle interior trim onto the windscreen. This phenomenon can be determined quantitatively in accordance with DIN 75201.

The use of reactive (instead of additive) flameproofing agents denotes a substantial improvement in this respect; in the case of polyurethanes, for example the use of phosphorus- and chlorine-containing polyols, which are reacted, by themselves or as a mixture with conventional polyols, with polyisocyanates and are thus bonded covalently into the polymer matrix.

DE-PS 20 36 587 describes a process for the preparation of phosphoric acid esters by successive reaction of phosphorus pentoxide and/or polyphosphoric acid with halogenated alkanols or phenols and with an epoxide. The products obtained by this process have the disadvantage that, to achieve the required flameproofing effectiveness, they comprise halogens in bonded form as an essential constituent. This is undesirable since, in the event of a fire, halogen-containing products can liberate corrosive hydrogen halides and, under certain circumstances, toxic decomposition products.

DE-OS 43 42 972 describes a process for the preparation of mixtures of oligomeric phosphoric acid esters which carry hydroxyalkoxy groups, in which orthophosphoric acid esters are reacted with phosphorus pentoxide, the P—O—P bonds in the polyphosphoric acid ester mixture obtained are partly hydrolyzed or glycolyzed selectively, and the mixture of polyphosphoric acid partial esters which is formed by this procedure is reacted with an epoxide. A disadvantage of this process is that relatively expensive trialkyl phosphates are employed as raw materials.

It is an object of the present invention to provide a simple and inexpensive process for the preparation of such phosphoric acid esters, by which products which are reactive (capable of incorporation) and halogen-free and at the same time have a high permanent flameproofing efficiency when employed in polyurethane foams are obtained.

This object is achieved by a process according to the precharacterizing clause of claim 1, which comprises reacting, in a first stage, aliphatic or araliphatic alcohols and/or phenols with phosphorus pentoxide ($P_4O_{10}$) in a molar ratio of (2.8 to 6.0):1.0 (alcohol/phenol:$P_4O_{10}$) at a temperature from 20° to 100° C. in the course of 0.5 to 72 hours, a polyphosphoric acid partial ester mixture of the formula (V)

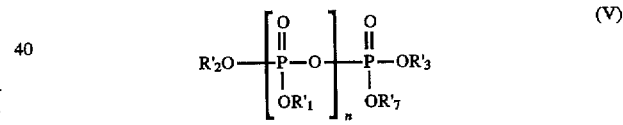

in which $R_1'$, $R_2'$, $R_3'$ and $R_7'$ are an alkyl or aryl radical or H, being obtained, and, in a second stage, reacting this mixture with an epoxide of the formula (IV)

in which $R_5$ and $R_6$ have the abovementioned meaning, at a temperature of 20°–180° C.

The molar ratio of alcohol/phenol:$P_4O_{10}$ is preferably (3.0–4.5):1.

The reaction in the first stage is preferably carried out at a temperature of 20° to 60° C.

The reaction in the first stage is preferably carried out in the course of 2 to 6 hours.

The reaction in the second stage is preferably carried out at a temperature of 60° to 100° C.

The ratio of groups which contain hydroxyl to groups which do not contain hydroxyl in the mixtures of the formula (I) is preferably about 1:1.

The oligomeric phosphoric acid esters prepared by the process according to the invention are used, above all, in polyurethane foams.

Preferred starting substances for the first process stage are methanol, ethanol, propanol, butanol, phenol and/or cresol.

Preferred epoxides of the formula (IV) are preferably those in which $R_5$ and $R_6$ are a hydrogen or methyl radical, in particular ethylene oxide and propylene oxide.

By varying the nature and ratios of amounts of the starting substances, the process of the invention allows the preparation of a broad spectrum of products. It is thus capable of meeting specific requirements, for example in respect of the average chain length, the hydroxyl number, the phosphorus content and the viscosity.

The mixtures of oligomeric phosphoric acid esters prepared by the process according to the invention comprise, for example, 0 to 65% by weight of compounds of the formula I where n=0, 0 to 50% by weight of compounds of the formula I where n=1, 0 to 50% by weight of compounds of the formula I where n=2, 0 to 50% by weight of compounds of the formula I where n=3, 0 to 45% by weight of compounds of the formula I where n=4 and 0 to 50% by weight of compounds of the formula I where n is >4, the sum being 100% by weight. Other numerical ratios can also be prepared accordingly.

EXAMPLE 1

166.5 g (5.2 mol) of methanol were initially introduced into a reactor fitted with a stirrer, thermometer, gas inlet tube and reflux condenser. With exclusion of atmospheric moisture and while stirring vigorously, 443 g (1.56 mol) of $P_4O_{10}$ were added such that the temperature did not rise above 40° C. The mixture was then heated at 80° C. for 6 hours. Ethylene oxide was passed into the brown-colored reaction mixture at a temperature 70° C. until severe reflux was to be observed in the condenser, which was charged with methanol and dry ice. After an after-reaction of 1 hour at 100° C., the ethylene oxide excess which remained was removed from the reaction mixture by passing through a vigorous stream of nitrogen.

1013 g of a pale yellowish liquid having a Brookfield viscosity of 3650 mPa.s (25° C.), an acid number of 0.3 mg of KOH/g, a hydroxyl number of 204 mg of KOH/g and a phosphorus content of 14.7% by weight were obtained. The mixture is composed of products of the formula (I) where n=0 (about 10% by weight), n=1 (about 20% by weight), n=2 (about 30% by weight), n=3 (about 20% by weight), n=4 (about 10% by weight) and n is >4 (about 10% by weight), in which in each case $R_1$ and $R_7$=methoxy and $R_5$ and $R_6$=H.

EXAMPLE 2

300 g (9.34 mol) of methanol were initially introduced into a reaction vessel analogous to Example 1. With exclusion of atmospheric moisture and while stirring vigorously, 443 g (1.56 mol) of $P_4O_{10}$ were added such that the temperature did not rise above 40° C. The mixture was then heated at 80° C. for 6 hours. Ethylene oxide was passed into the brown-colored reaction mixture at a temperature of 70° C. until severe reflux was to be observed in the condenser, which was charged with methanol and dry ice. After an after-reaction of 1 hour at 100° C., the ethylene oxide excess which remained was removed from the reaction mixture by passing through a vigorous stream of nitrogen. 1800 g of a pale yellowish liquid having a Brookfield viscosity of 170mPa.s (25° C.), an acid number of 0.3 mg of KOH/g, a hydroxyl number of 260 mg of KOH/g and a phosphorus content of 10.2% by weight were thus obtained. The mixture is composed of products of the formula (I) where n=0 (about 60% by weight), n=1 (about 20% by weight), n=2 (about 10% by weight) and n is >2 (about 10% by weight), in which in each case $R_1$ and $R_7$=methoxy and $R_5$ and $R_6$=H.

EXAMPLE 3

300 g (6.52 mol) of ethanol were initially introduced into a reaction vessel analogous to Example 1. With exclusion of atmospheric moisture and while stirring vigorously, 460 g (1.61 mol) of $P_4O_{10}$ were added such that the temperature did not exceed 40° C. The mixture was then heated at 80° C. for 4 hours. Ethylene oxide was passed into the brown-colored reaction mixture at a temperature of 70° C. until severe reflux was to be observed in the condenser, which was charged with methanol and dry ice. After an after-reaction of 1 hour at 100° C., the ethylene oxide excess which remained was removed from the reaction mixture bypassing through a vigorous stream of nitrogen. 1500 g of a pale yellowish liquid having a Brookfield viscosity of 500 mPa.s (25° C.), an acid number of 0.6 mg of KOH/g, a hydroxyl number of 200 mg of KOH/g and a phosphorus content of 13.8% by weight were thus obtained. The mixture is composed of products of the formula (I) where n=0 (about 20% by weight), n=1 (about 40% by weight), n=2 (about 15% by weight), n=3 (about 10% by weight) and n is >3 (about 15% by weight), in which in each case $R_1$ and $R_7$=ethoxy and $R_5$ and $R_6$=H.

EXAMPLE 4

319 g (6.9 mol) of ethanol were reacted with 596.4 g (2.1 mol) of $P_4O_{10}$ and ethylene oxide in accordance with the instructions given in Example 1 in a reaction vessel analogous to Example 1. 1700 g of a pale yellowish liquid having a Brookfield viscosity of 2100 mPa.s (25° C.), an acid number of 0.5 mg of KOH/g, a hydroxyl number of 200 mg of KOH/g and a phosphorus content of 14.3% by weight were thus obtained. The mixture is composed of products of the formula (I) where n=0 (about 10% by weight), n=1 (about 20% by weight), n=2 (about 30% by weight), n=3 (about 20% by weight), n=4 (about 10% by weight) and n is >4 (about 10% by weight), in which in each case $R_1$ and $R_7$=ethoxy and $R_5$ and $R_6$=H.

EXAMPLE 5

164 g (2.2 mol) of butanol were reacted with 188.6 g (0.66 mol) of $P_4O_{10}$ and ethylene oxide in accordance with the instructions given in Example 1 in a reaction vessel analogous to Example 1. 510 g of a pale yellowish liquid having a Brookfield viscosity of 580 mPa.s (25° C.), an acid number of 0.5 mg of KOH/g, a hydroxyl number of 180 mg of KOH/g and a phosphorus content of 13.1% by weight were thus obtained. The mixture is composed of products of the formula (I) where n=0 (about 10% by weight), n=1 (about 20% by weight), n=2 (about 30% by weight), n=3 (about 20% by weight), n=4 (about 10% by weight) and n is >4 (about 10% by weight), in which in each case $R_1$ and $R_7$=butoxy and $R_5$ and $R_6$=H.

EXAMPLE 6

The product according to Example 1 was incorporated into a flexible polyurethane foam of the following formulation (parts=parts by weight):

| 100 parts | ® Caradol 46-3 (polyether-polyol, Shell) |
|---|---|
| 7.5 parts | product from Example 1 |
| 4.0 parts | water |
| 0.4 part | dimethylethanolamine |
| 0.2 part | ® Desmorapid SO (Bayer) |
| 1.0 part | ® Tegostab B 3640 (Goldschmidt) |
| 51 parts | toluylene diisocyanate ( ® Desmodur T 80, Bayer) |

To produce the test foam, all the components—with the exception of the toluylene diisocyanate—were mixed intensively, and ®Desmodur T 80 was then added.

After a cream time of 15 seconds, a rising time of 150 seconds and an after-treatment of 15 minutes at 140° C.

ambient air, a flexible polyurethane foam having a density of 29 kg/m³ was obtained.

To determine the flame resistance of the test foam according to Examples 6 and 7, the oxygen index (LOI) was determined in accordance with ASTM-D-2863-77 and the American test FMVSS-302 (FMVSS=Federal Motor Vehicle Safety Standard) was carried out.

An oxygen index of 0.22 was found. In the FMVSS 302 burning test, the best class SE (self-extinguishing) was achieved with an average burning distance of 23 mm.

The foam was tested in respect of fogging properties in accordance with DIN 75201-G. A condensate of only 0.6 mg was found.

EXAMPLE 7

The product according to Example 3 was incorporated into a rigid polyurethane foam of the following formulation (parts by weight):

| 100 parts | ® Caradol 585 (polyether-polyol, Shell) |
| 25 parts | product from Example 3 |
| 3.0 parts | water |
| 2.5 parts | dimethylcyclohexylamine |
| 2.0 parts | ® DC 193 (silicone stabilizer, Dow Corning) |
| 15 parts | Blowing agent R 41 b |
| 214 parts | polyisocyanate (® Caradate 30, Shell) |

To evaluate the flame retardancy, the small burner test according to DIN 4102 Part 1 was carried out. The foam according to Example 7 with a gross density of 33 kg/m³ achieves class B 2 in this test. If the halogen-containing additive tris(2-chloropropyl) phosphate (TCPP) used industrially is used, this class can be achieved only if an amount of 30 parts is employed.

This result clearly shows the outstanding suitability of the products prepared according to the invention in respect of their use as reactive flameproofing agents for flexible polyurethane foams and rigid polyurethane foams.

I claim:

1. A process for the preparation of a mixture of oligomeric phosphoric acid esters of the formula (I)

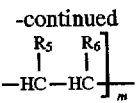 (I)

in which n is a number from 0 to 8, $R_1$, $R_2$, $R_3$ and $R_7$ are identical or different and are a halogen-free alkyl or aryl radical or a hydroxyl-containing radical of the formula II and $R_4$ is a radical of the formula III

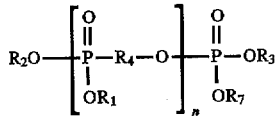 (II)

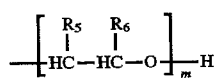 (III)

in which, in the formulae II and III, $R_5$ and $R_6$ are a hydrogen atom or an alkyl radical and m is a number from 1 to 4, which comprises reacting, in a first stage, aliphatic or araliphatic alcohols and/or phenols with phosphorus pentoxide ($P_4O_{10}$) in a molar ratio of (2.8 to 6.0):1.0 (alcohol/phenol:$P_4O_{10}$) at a temperature from 20° to 100° C. in the course of 0.5 to 72 hours, a polyphosphoric acid partial ester mixture of the formula V

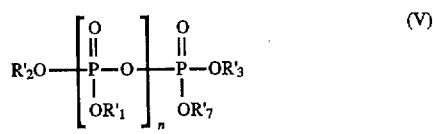 (V)

in which $R_1'$, $R_2'$, $R_3'$ and $R_7'$ are an alkyl or aryl radical or H, being obtained, and, in a second stage, reacting this mixture with an epoxide of the formula (IV)

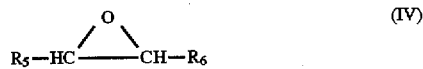 (IV)

at a temperature of 20°–180° C.

2. The process as claimed in claim 1, wherein the molar ratio is (3.0–4.5):1.

3. The process as claimed in claim 1, wherein the reaction in the first stage is carried out at a temperature of 20° to 60° C.

4. The process as claimed in at least claim 1, wherein the reaction in the first stage is carried out in the course of 2 to 6 hours.

5. The process as claimed in at least claim 1, wherein the reaction in the second stage is carried out at a temperature of 60° to 100° C.

6. The process as claimed in at least claim 1, wherein the ratio of groups which contain hydroxyl to groups which do not contain hydroxyl is about 1:1.

7. A polyurethane foam which contains a mixture of oligomeric phosphoric acid esters prepared as claimed in claim 1.

8. A polyurethane foam which contains a mixture of oligomeric phosphoric acid esters prepared as claimed in claim 2.

9. A polyurethane foam which contains a mixture of oligomeric phosphoric acid esters prepared as claimed in claim 3.

10. A polyurethane foam which contains a mixture of oligomeric phosphoric acid esters prepared as claimed in claim 4.

11. A polyurethane foam which contains a mixture of oligomeric phosphoric acid esters prepared as claimed in claim 5.

12. A polyurethane foam which contains a mixture of oligomeric phosphoric acid esters prepared as claimed in claim 6.

* * * * *